United States Patent
Löffler et al.

[11] Patent Number: 5,952,283
[45] Date of Patent: Sep. 14, 1999

[54] QUATERNARY AMMONIUM COMPOUNDS AS BLEACH ACTIVATORS AND THEIR PREPARATION

[75] Inventors: Matthias Löffler, Niedernhausen; Gerd Reinhardt, Kelkheim, both of Germany

[73] Assignee: Clariant GmbH, Frankfurt, Germany

[21] Appl. No.: 09/131,457

[22] Filed: Aug. 10, 1998

Related U.S. Application Data

[62] Division of application No. 08/881,661, Jun. 24, 1997, Pat. No. 5,877,325.

[30] Foreign Application Priority Data

Jun. 26, 1996 [DE] Germany ............... 196 25 495

[51] Int. Cl.$^6$ ............... C11D 3/00; C11D 3/395; C11D 7/54; C11D 9/00
[52] U.S. Cl. ............... 510/376; 510/220; 510/238; 510/312; 510/407; 510/504
[58] Field of Search .................... 510/312, 376, 510/367, 504, 407, 220, 238

[56] References Cited

U.S. PATENT DOCUMENTS

| | | | |
|---|---|---|---|
| 2,945,863 | 7/1960 | Buc et al. | 260/326.3 |
| 3,945,897 | 3/1976 | Choi | 204/158 HA |
| 4,299,769 | 11/1981 | McEvoy et al. | 260/326.35 |
| 4,397,757 | 8/1983 | Bright et al. | 252/186.41 |
| 4,732,990 | 3/1988 | Login et al. | 548/550 |
| 4,751,015 | 6/1988 | Humphreys et al. | 252/99 |
| 4,933,103 | 6/1990 | Aoyagi et al. | 252/186.38 |
| 5,008,104 | 4/1991 | Chaudhuri et al. | 424/70 |
| 5,047,577 | 9/1991 | Smith et al. | 560/253 |
| 5,241,077 | 8/1993 | Oakes et al. | 548/477 |
| 5,460,747 | 10/1995 | Gosselink et al. | 252/186.38 |
| 5,560,862 | 10/1996 | Gosselink et al. | 252/186.39 |
| 5,578,136 | 11/1996 | Taylor et al. | 139/25.2 |
| 5,599,781 | 2/1997 | Haeggberg et al. | 510/220 |
| 5,685,015 | 11/1997 | Willey et al. | 252/186.29 |
| 5,827,813 | 10/1998 | Hartman et al. | 510/443 |
| 5,877,325 | 3/1999 | Loffler et al. | 548/333.5 |

FOREIGN PATENT DOCUMENTS

WO 92/21656  12/1992  WIPO.

*Primary Examiner*—Mark Kopec
*Assistant Examiner*—John M Petruncio
*Attorney, Agent, or Firm*—Miles B. Dearth

[57] ABSTRACT

Quaternary ammonium compounds, their preparation and use Compounds of the formula I

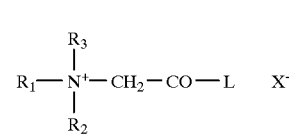

are claimed, as are their preparation and use, in which the radicals $R_1$, $R_2$ and $R_3$ are organic substituents, L is either a lactam or a cyclic amidine and X is an appropriate anion. The novel compounds are employed as bleach activators in cleaners and detergents which have a bleaching action.

12 Claims, No Drawings

QUATERNARY AMMONIUM COMPOUNDS AS BLEACH ACTIVATORS AND THEIR PREPARATION

This is a divisional of application Ser. No. 08/881,661 filed on Jun. 24, 1997, now U.S. Pat. No. 5,877,325.

This invention relates to quaternary ammonium compounds, to their preparation and to detergent compositions which include these quaternary ammonium compounds as bleach activators.

It is known that the bleaching power of peroxide bleaches such as perborates, percarbonates, persilicates and perphosphates can be improved so that bleaching begins at lower temperatures, for instance at or below 60° C., by adding the precursors of bleaching peroxy acids, which are often referred to as bleach activators.

Numerous substances are known in the prior art as bleach activators. They are usually reactive organic compounds with an O-acyl or N-acyl group, which combine in alkaline solution with a source of hydrogen peroxide to form the corresponding peroxy acids.

Representative examples of bleach activators are for instance N,N,N',N'-tetraacetylethylenediamine (TAED), glucose pentaacetate (GPA), xylose tetraacetate (TAX), sodium 4-benzoyloxybenzenesulfonate (SBOBS), sodium trimethylhexanoyloxybenzenesulfonate (STHOBS), tetraacetylglycoluril (TAGU), tetraacetylcyanic acid (TACA), di-N-acetyldimethylglyoxine (ADMG) and 1-phenyl-3-acetylhydantoin (PAH). Reference may be made, for example, to GB-A-836 988, GB-A-907 356, EP-A-0 098 129 and EP-A-0 120 591.

Over time, cationic peroxy acid precursors containing for example, in addition to O-acyl or N-acyl groups, a quaternary ammonium group have gained in importance because they are highly effective bleach activators. Cationic peroxy acid precursors of this kind are described, for example, in U.S. Pat. No. 5,460,747, U.S. Pat. No. 5,047,577, U.S. Pat. No. 4,933,103, U.S. Pat. No. 4,751,015, U.S. Pat. No. 4,397,757, GB-1 382 594, WO-95 21150, EP-A-403 152, EP-A-427 224, EP-A-402 971, EP-371 809 and EP-A-284 292. Corresponding free, stable quaternary peracids are described, for example, in EP-A-340 754 and WO-94 01399.

It has surprisingly now been found that certain quaternary bleach activators as described below have a better bleaching action than the prior art bleach activators. In addition, the novel bleach activators can be prepared with fewer synthesis steps, and therefore in a more ecologically and economically favorable manner, than the prior art bleach activators.

The invention provides compounds of the formula I

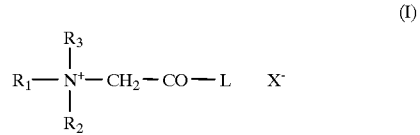

(I)

in which a) $R_1$, $R_2$ and $R_3$ independently of one another are $C_1$- to $C_{24}$-alkyl, aryl, $C_2$–$C_{24}$-alkenyl, $C_1$–$C_4$-alkoxy-$C_1$–$C_4$-alkyl, or $CH_2$—CO—L, or b) $R_2$ and $R_3$, together with the nitrogen atom to which they are attached, form a ring having from 4 to 6 carbon atoms, which ring may in addition to the nitrogen atom contain, in place of carbon atoms, one or two oxygen atoms or a group

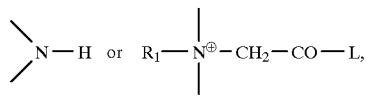

L is a group of the formula

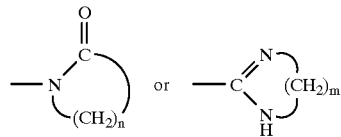

n is a number from 3 to 5, m is a number from 2 to 4 and X is an anion.

Preferred anions are chloride, bromide, iodide, fluoride, sulfate, hydrogen sulfate, carbonate, hydrogen carbonate, phosphate, mono- and dihydrogen phosphate, pyrophosphate, metaphosphate, nitrate, methosulfate, dodecyl sulfate, dodecylbenzenesulfonate, phosphonate, methylphosphonate, methanedisulfonate, methylsulfonate, ethanesulfonate and p-toluenesulfonate.

The substituents $R_1$, $R_2$ and $R_3$ independently of one another are preferably unsubstituted $C_1$–$C_4$-alkyl, unsubstituted $C_2$–$C_4$-alkenyl or phenyl. L is preferably a pyrrolidone group.

Particular preference is given to short-chain (trialkylammonium)acetylpyrrolidone chlorides and corresponding (trialkylammonium)acetyl-imidazole chlorides with $C_1$- to $C_4$-alkyl groups, especially 2-(N,N,N-trimethylammonium)acetylpyrrolidone chloride, 2-(N,N,N-triethylammonium)acetylpyrrolidone chloride, 2-(N,N-diethyl-N-methylammonium)acetylpyrrolidone chloride, and the corresponding imidazole derivatives.

The invention additionally provides a process for preparing these compounds. The general examples below will be used to illustrate the synthesis pathways leading to the novel cationic bleach activators.

GENERAL EXAMPLE 1

A lactam and an appropriate auxiliary base are charged in an organic solvent to a reactor. Chloroacetyl chloride is added dropwise, with cooling, at temperatures between 0 and 30° C., preferably at 5° C. After a reaction period of from 3 to 12 hours at temperatures between 10 and 30° C., preferably at 25° C., the resulting precipitate is filtered off. The subsequent reaction can proceed without isolation of the resulting N-(chloroacetyl)amide beforehand. Following the addition of a tertiary amine, reaction is carried out at temperatures of between 20 and 100° C., preferably between 70 and 80° C., to give the corresponding 2-(N,N,N-trialkylammonium)acetyllactam chloride. In the case of the short-chain amines preferably employed, the reaction is carried out in an autoclave if desired.

GENERAL EXAMPLE 2

A lactam and an appropriate auxiliary base are charged in an organic solvent to a reactor. Chloroacetyl chloride is added dropwise, with cooling, at temperatures between 0 and 30° C., preferably at 5° C. After a reaction period of from 3 to 12 hours at temperatures between 10 and 30° C., preferably at 25° C., the resulting precipitate is filtered off.

The subsequent reaction can proceed without isolation of the resulting N-(chloroacetyl)amide beforehand. At temperatures between 0 and 50° C., preferably with cooling at 20° C., a secondary amine is added. Following a reaction period of from 3 to 12 hours at temperatures of between 10 and 50° C., preferably at 25° C., the resulting precipitate is filtered off. With no need to isolate the resulting intermediate beforehand, the 2-(N,N-dialkylamine) acetyllactam obtained is reacted with an alkylating agent such as methyl chloride or dimethyl sulfate at temperatures of between 20 and 100° C., preferably between 70 and 80° C., to give the corresponding 2-(N,N,N-trialkylammonium)acetyllactam salt.

The auxiliary base used is preferably the amines employed for the reaction.

The invention also provides bleaching detergents and cleaners (cleaning compositions) which comprise the novel compounds as bleach activators. These detergents and cleaners commonly, in addition to a peroxy compound and the cationic bleach activator, include surface-active compounds and other ingredients as well.

Suitable peroxy compounds are alkali metal peroxides, organic peroxides such as urea peroxide, and inorganic per salts, such as the perborates, percarbonates, perphosphates, persilicates and persulfates of alkali metals. Mixtures of two or more of these compounds are likewise suitable. Particular preference is given to sodium perborate tetrahydrate and, in particular, to sodium perborate monohydrate. Sodium perborate monohydrate is preferred on account of its good stability on storage and its ready solubility in water. Sodium percarbonate may be preferred on environmental grounds.

Alkyl hydroperoxides constitute a further suitable group of peroxy compounds. Examples of these substances are cumene hydroperoxide and t-butyl hydroperoxide.

In detergents and cleaners of this kind the content by weight of the novel cationic bleach activator can be from about 0.1% to 20%, preferably from 0.5% to 10%, in particular from 1% to 7.5%, together with a peroxy compound. The proportion by weight of these peroxy compounds is commonly from 2% to 40%, preferably from 4% to 30%, in particular from 10% to 25%.

The detergents and cleaners may also, in addition to the novel cationic bleach activators, include other suitable bleach activators, such as TAED, for example.

The surface-active substance can be derived from natural products, such as soap, or can be a synthetic compound from the group consisting of anionic, nonionic, amphoteric, zwitterionic and cationic surface-active substances or mixtures thereof. Numerous suitable substances are commercially available and are described in the literature, for example in "Surface active agents and detergents", Vol. 1 and 2, by Schwartz, Perry and Berch. The overall proportion of the surface-active compounds can be up to 50% by weight, preferably from 1% by weight to 40% by weight, in particular from 4% by weight to 25% by weight.

Synthetic anionic surface-active substances are usually water-soluble alkali metal salts of organic sulfates and sulfonates with alkyl radicals of about 8 to 22 carbon atoms, the term "alkyl" including the alkyl substituents of higher aryl radicals.

Examples of suitable anionic detergents are sodium and ammonium alkyl sulfates, especially the sulfates obtained by sulfation of higher ($C_8$ to $C_{18}$) alcohols; sodium and ammonium alkylbenzenesulfonates having an alkyl radical of $C_9$ to $C_{20}$, especially linear secondary sodium alkylbenzenesulfonates having an alkyl radical of $C_{10}$ to $C_{15}$; sodium alkyl glycerol ether sulfates, especially the esters of the higher alcohols derived from tallow oil and coconut oil; the sodium sulfates and sulfonates of the coconut fatty acid monoglycerides; sodium and ammonium salts of the sulfuric acid esters of higher ($C_9$ to $C_{18}$) alkoxylated fatty alcohols, especially those alkoxylated with ethylene oxide; the reaction products of the esterification of fatty acids with isethionic acid followed by neutralization with sodium hydroxide; sodium and ammonium salts of the fatty acid amides of methyltaurine; alkanemonosulfonates, such as those from the reaction of α-olefins ($C_8$–$C_{20}$) with sodium bisulfite and those from the reaction of paraffins with $SO_2$ and $Cl_{20}$ followed by basic hydrolysis, giving a mixture of different sulfonates; sodium and ammonium dialkyl sulfosuccinates with alkyl radicals of $C_7$ to $C_{12}$; and olefinsulfonates which are formed in the reaction of olefins, especially $C_{10}$ to $C_2$ α-olefins, with $SO_3$ followed by hydrolysis of the reaction products. The preferred anionic detersives are sodium alkylbenzenesulfonates with alkyl radicals of $C_{15}$ to $C_{18}$, and sodium alkyl ether sulfates with alkyl radicals of $C_{16}$ to $C_{18}$.

Examples of suitable nonionic surface-active compounds which are used preferably together with anionic surface-active compounds are, in particular, the reaction products of alkylene oxides (commonly ethylene oxide) with alkylphenols (alkyl radicals of $C_5$ to $C_{22}$), the reaction products generally containing from 5 to 25 ethylene oxide (EO) units within the molecule; the reaction products of aliphatic ($C_8$ to $C_{18}$) primary or secondary, linear or branched alcohols with ethylene oxide, generally with from 6 to 30 EO, and the adducts of ethylene oxide with reaction products of propylene oxide and ethylenediamine. Other nonionic surface-active compounds are alkylpolyglycosides, long-chain tertiary amine oxides, long-chain tertiary phosphine oxides and dialkyl sulfoxides.

Amphoteric or zwitterionic surface-active compounds can likewise be used in the novel compositions, although this is usually not desirable owing to their high cost. If amphoteric or zwitterionic compounds are used, they are generally employed in small amounts in compositions which predominantly comprise anionic and nonionic surfactants.

Soaps as well can be used in the novel compositions, preferably in a proportion of less than 25% by weight. They are particularly suitable in small amounts in binary (soap/anionic surfactant) or in ternary mixtures together with nonionic or mixed synthetic anionic and nonionic surfactants. The soaps used are preferably the sodium salts, and less preferably the potassium salts, of saturated or unsaturated $C_{10}$ to $C_{24}$ fatty acids, or mixtures thereof. The proportions of such soaps can be from 0.5% by weight to 25% by weight; smaller amounts of from 0.5% by weight to 5% by weight are generally sufficient for foam control. Proportions of soaps of between about 2% and about 20%, in particular between about 5% and about 10%, have a positive effect. This is especially the case in hard water, where the soap acts as an additional builder substance.

The detergents and cleaners generally also include a builder. Suitable builders are calcium-binding substances, precipitants, calcium-specific ion exchangers and mixtures thereof. Examples of calcium-binding substances include alkali metal polyphosphates, such as sodium tripolyphosphate; nitrilotriacetic acid and its water-soluble salts; the alkali metal salts of carboxymethyloxysuccinic acid, ethylenediaminetetraacetic acid, oxydisuccinic acid, mellitic acid, benzenepolycarboxylic acids and citric acid; and polyacetyl carboxylates, as disclosed in U.S. Pat. No. 4,144,226 and U.S. Pat. No. 4,146,495.

Examples of precipitants include sodium orthophosphate, sodium carbonate and soaps of long-chain fatty acids.

Examples of ion exchangers which are specific for calcium include the various types of water-insoluble, crystalline or amorphous aluminum silicates, of which the zeolites are the best-known representatives.

These builder substances can be present in a proportion of from 5% by weight to 80% by weight, preferably from 10% by weight to 60% by weight.

In addition to the ingredients already mentioned, the detergents and cleaners may include any of the conventional additives in amounts which are customary in such compositions. Examples of these additives include foam formers, such as alkanolamides, especially the monoethanolamides of palm kernel oil fatty acids and coconut fatty acids; foam inhibitors, such as alkyl phosphates and alkylsilicones; graying inhibitors (antiredeposition agents) and similar auxiliaries, such as sodium carboxymethylcellulose and alkyl- or substituted alkylcellulose ethers; stabilizers, such as ethylenediaminetetraacetic acid; softeners for textiles; inorganic salts, such as sodium sulfate; and, in usually small amounts, fluorescent substances, fragrances, enzymes such as proteases, cellulases, lipases and amylases, disinfectants and colorants. The bleach activators of this invention can be employed in a large number of products. Such products include textile detergents, textile bleaches, surface cleaners, toilet cleaners, dishwasher detergents, and also denture cleansers. The detergents can be in solid or liquid form.

For reasons of stability and ease of handling it is advantageous to use the bleach activators in the form of granules which in addition to the bleach activator include a binder. Various methods of preparing such granules are described in the patent literature, for example in CA-1 102 966, GB-1 561 333, U.S. Pat. No. 4,087,369, EP-A-0 240 057, EP-A-0 241 962, EP-A-0 101 634 and EP-A-0 062 523. Any of these methods can be employed for the novel bleach activators.

The granules containing the bleach activators are generally added to the detergent composition together with the other dry constituents, such as enzymes, inorganic peroxide bleaches, etc. The detergent composition to which the activator granules are added can be obtained by various methods, such as dry mixing, extrusion or spray drying.

In a further embodiment the novel bleach activators are particularly suitable for nonaqueous liquid detergents, together with a bleaching peroxy compound, for instance sodium perborate, in order to give the detergent a high cleaning capacity for fabrics and textiles. Nonaqueous liquid detergents of this kind, which include pasty and gelatinous detersive compositions, are known in the prior art and are described, for example, in U.S. Pat. No. 2,864,770, U.S. Pat. No. 2,940,938, U.S. Pat. No. 4,772,412, U.S. Pat. No. 3,368,977, GB-A-1205 711, GB-A-1 370 377, GB-A-1 270 040, GB-A-1 292 352, GB-A-2 194 536, DE-A-2 233 771 and EP-A-0 028 849.

These compositions are in the form of a nonaqueous liquid medium in which a solid phase may be dispersed. The nonaqueous liquid medium can be a liquid, surface-active substance, preferably a nonionic surface-active substance; a nonpolar liquid medium, such as liquid paraffin; a polar solvent, for instance polyols, for example glycerol, sorbitol, ethylene glycol, alone or in conjunction with low molecular mass monofunctional alcohols such as ethanol or isopropanol; or mixtures thereof.

The solid phase may consist of builder substances, alkalis, abrasive substances, polymers, other solid ionic surface-active substances, bleaches, fluorescent substances, and other customary solid ingredients.

The following examples are intended to give an overview of the embodiments of the invention.

EXAMPLE 1 a) Synthesis of N-(chloroacetyl)pyrrolidone

To an initial charge of 81.0 g of 2-pyrrolidone in 200 ml of toluene there are added, dropwise and with ice cooling, 54.7 g of chloroacetyl chloride such that the temperature of the reaction mixture remains at 5° C. Following the addition the reaction mixture is stirred at room temperature for 6 hours. The resulting precipitate is filtered off with suction and the solvent is removed in vacuo to give 74.5 g of N-(chloroacetyl)pyrrolidone, corresponding to a yield of 97%.

b) Synthesis of 2-(N,N-diethylamine)acetylpyrrolidone

To 80.0 g of (chloroacetyl)pyrrolidone dissolved in 200 ml of toluene there are added, dropwise and with ice cooling, 73.1 g of diethylamine, so that the temperature of the reaction mixture does not exceed 50° C. After the addition the reaction mixture is cooled to room temperature and is stirred at this temperature for 2 hours more. The resulting precipitate is filtered off with suction and the solvent is removed in vacuo to give 74.9 g of 2-(N,N-diethylamine) acetylpyrrolidone, corresponding to a yield of 76%.

c) Synthesis of 2-(N,N-diethyl-N-methylammonium) acetylpyrrolidone tosylate (Compound No. 1)

To 19.8 g of 2-(N,N-diethylamine)acetylpyrrolidone in 30 ml of acetonitrile there are added, dropwise, 73.1 g of methyl 4-toluenesulfonate. After the addition the mixture is refluxed for 3 hours and then the solvent is removed in vacuo to give a highly viscous oil which after recrystallization from isopropanol is obtained in the form of colorless crystals. The yield of 2-(N,N-diethyl-N-methylammonium) acetylpyrrolidone tosylate is 33.5 g, corresponding to a yield of 87%.

Compounds 2 and 3 were prepared analogously (see page 13).

EXAMPLE 2

The combination of 200 ml of an aqueous solution of 5 g/l reference detergent (WMP) obtained from WFK-Testgewebe GmbH, Krefeld, 150 mg of sodium perborate monohydrate (PB*1) and 50 mg of an activator gave a bleaching composition. Four pieces of fabric soiled with black tea (BC-1 tea on cotton, 1.25 g, WFK) were added for a thirty-minute isothermal washing experiment in a Linitest apparatus. After the predetermined washing time, the pieces of fabric were rinsed with water, dried and ironed. The bleaching action was then determined by means of an ELREPHO 2000 whiteness meter (Datacolor) by determining the differences in reflectance before and after bleaching.

Comparison experiments were carried out in which 50 mg of a novel activator were added in addition to the detergent composition. The investigations were repeated with different types of soiling (e.g. red wine, curry).

Bleach compositions with the bleach activators 1 to 3 were prepared. Their effectiveness was determined by comparing the reflectances of the fabric before and after the bleaching process. The results are indicated in Table 1. The $\Delta\Delta R$ values indicate the improvement in the bleaching action of the novel composition compared with PB*1:

$$\Delta\Delta 6R\ (QUAT-PB^*1) = \Delta R\ (QUAT) - \Delta R\ (PB^*1)$$

The compounds 1 to 3 are

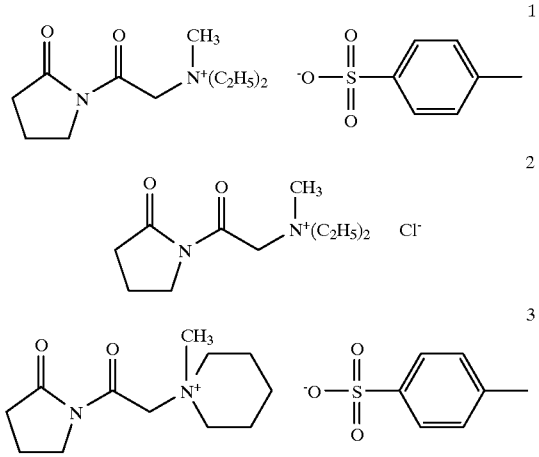

TABLE 1

| Activator No. | Δ R (QUAT) | ΔΔ R (QUAT-PB*1) |
|---|---|---|
| | Tea, 40° C. | |
| PB*1 | 7.8 | |
| 1 | 10.7 | 2.9 |
| 2 | 12.3 | 4.5 |
| 3 | 10.1 | 2.3 |
| | Red Wine, 40° C. | |
| PB*1 | 15.1 | |
| 1 | 18.2 | 3.1 |
| 2 | 19.8 | 4.7 |
| 3 | 17.1 | 2.0 |

The washing experiments show that the bleach compositions which include novel bleach activators give better washing results than the comparison detergent which lacks novel bleach activators.

We claim:

1. A detergent or cleaner comprising
   a) from 2 to 40% by weight of a peroxy compound; and
   b) from 0.1 to 20% by weight of a compound of the formula (I)

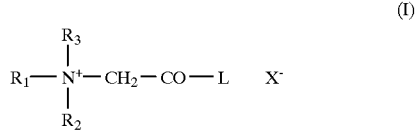

as bleach activator wherein
   a) $R_1$, $R_2$ and $R_3$ independently of one another are $C_1$- to $C_{24}$-alkyl, aryl, $C_2$–$C_{24}$-alkenyl, $C_1$–$C_4$-alkoxy-$C_1$–$C_4$-alkyl, or $CH_2$—CO—L, or
   b) $R_2$ and $R_3$, together with the nitrogen atom to which they are attached, form a heterocyclic ring having from 4 to 6 carbon atoms, or form a heterocyclic ring having from 2 to 5 carbon atoms and 1 to 2 oxygen atoms, or a group

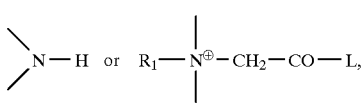

L is a group of the formula

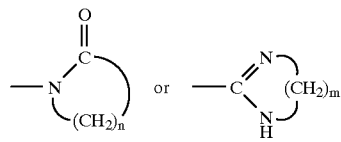

n is a number from 3 to 5,
m is a number from 2 to 4, and
X is an anion.

2. The detergent or cleaner as claimed in claim 1, wherein the peroxy compound is present in an amount of from 4 to 30% by weight.

3. The detergent or cleaner as claimed in claim 2, wherein the peroxy compound is present in an amount of from 10 to 25% by weight.

4. The detergent or cleaner as claimed in claim 1, wherein the bleach activator is present in an amount of from 0.5 to 10% by weight.

5. The detergent or cleaner as claimed in claim 4, wherein the bleach activator is present in an amount of from 1 to 7.5% by weight.

6. The detergent or cleaner as claimed in claim 1, wherein the per compound is an inorganic material selected from the group consisting of perborate, percarbonate, perphosphate, persilicate, and monopersulfate.

7. The detergent or cleaner as claimed in claim 1, wherein the per compound is an organic material selected from the group consisting of urea peroxide, cumene hydroperoxide and t-butyl hydroperoxide.

8. The detergent or cleaner as claimed in claim 1, which further comprises from 1 to 80% of a detergent builder.

9. The detergent or cleaner as claimed in claim 1, which further comprises an enzyme selected from the group consisting of proteases, cellulases, lipases, amylases and mixtures thereof in an amount which is effective for cleaning.

10. The detergent or cleaner as claimed in claim 1, which further comprises surface-active substances to be present in an amount of up to 50% by weight.

11. The detergent or cleaner as claimed in claim 1, which further comprises soaps to be present in an amount of up to 25% by weight.

12. The detergent or cleaner as claimed in claim 8, which comprises the builder in an amount of from 5 to 80% by weight.

* * * * *